United States Patent [19]

Gust

[11] Patent Number: 4,973,165

[45] Date of Patent: Nov. 27, 1990

[54] METHOD OF GENERATING PRECISELY-DEFINED WALL SHEARING STRESSES

[75] Inventor: Giselher R. Gust, St. Petersburg, Fla.

[73] Assignee: Hydro Data, Inc., St. Petersburg, Fla.

[21] Appl. No.: 419,649

[22] Filed: Oct. 11, 1989

Related U.S. Application Data

[62] Division of Ser. No. 194,396, May 16, 1988, Pat. No. 4,884,892.

[30] Foreign Application Priority Data

May 27, 1987 [DE] Fed. Rep. of Germany ... 3717969.

[51] Int. Cl.$^5$ .............................................. B01F 7/26
[52] U.S. Cl. ........................................ 366/2; 366/136; 366/168; 366/315
[58] Field of Search ............... 366/2, 168, 191, 194, 366/279, 262, 263, 136, 137, 315, 247, 249

[56] References Cited

U.S. PATENT DOCUMENTS

| | | | |
|---|---|---|---|
| 565,817 | 8/1896 | Walker, Jr. | 366/164 |
| 805,710 | 11/1905 | Cheney | 366/164 |
| 1,155,306 | 9/1915 | Fay | 366/164 |
| 3,254,877 | 6/1966 | Goodwin | 366/137 |
| 3,278,295 | 10/1966 | Ostberg et al. | 366/262 |
| 3,595,547 | 7/1971 | Polomsky et al. | 366/262 X |
| 4,534,654 | 8/1985 | Alt et al. | 366/137 |
| 4,534,655 | 8/1985 | King et al. | 366/137 |

*Primary Examiner*—Frankie L. Stinson
*Attorney, Agent, or Firm*—Herbert W. Larson

[57] ABSTRACT

A method is provided to generate over a confined space precisely defined distributions of the magnitude of the wall shearing stresses in a substrate/fluid boundary layer. A fluid flow is rotated around a center axis in the confined space. Simultaneously a defined fluid volume is removed in the rotational axis of the flow per unit time and recirculated or replenished through return openings in the lid or sidewall.

8 Claims, 3 Drawing Sheets

METHOD OF GENERATING PRECISELY-DEFINED WALL SHEARING STRESSES

PRIOR APPLICATIONS

This application is a divisional continuation-in-part from my allowed prior application S.N. 07/194,396, filed May 16, 1988 now U.S. Pat. No. 4,884,892.

BACKGROUND OF THE INVENTION

1. Field of the Invention

The invention relates to methods for causing the mixing of substances and fluids at interfaces with varying density gradients. More particularly the invention describes a method of generating precisely-defined wall shearing stresses at a substrate/fluid interface, especially those of a sediment/water interface within a confined space, together with an apparatus to realize this method.

2. Description of the Prior Art

Wall shearing stresses play a pivotal role in hydrodynamical, sedimentological, biological, geochemical, and engineering processes and their control at substrate/fluid interfaces. The investigation of sediment/water boundary layers in rivers, lakes and oceans is of great importance; e.g., the determination of the vertical exchange (flux) of chemical substances between sediment and overlying water, the entrainment of sediment eroded off the bottom, or the determination of porewater concentration profiles as well as the reservoir capacity of sediments for chemical substances including adsorbed pollutants. The latter concerns waste disposal, pathways of toxins and environmental health. In order to achieve realistic results in these areas, it is mandatory to establish quantitatively the link between the studied process and the wall shearing stresses acting at the substrate/fluid interface. To achieve this goal a flow pattern in the fluid has to be generated which produces precisely known wall shearing stresses at the substrate/fluid boundary layer.

The generation of a boundary layer structure homogeneous over a relatively large surface area between a substrate and overlying fluid with a resulting spatially homogeneous distribution of the wall shearing stress over the whole area can be relevant also for industrial processing and manufacturing techniques, especially in microbiological manufacturing techniques, titration processes, surface coatings, and others. It is also useful in establishing the best possible growth environment for bacterial cultures or to optimize their exudates.

The invention has thus the task to find an engineering procedure as well as an apparatus which permits the generation of precisely defined wall shearing stress fields in a substrate/fluid boundary layer within a confined measuring volume for steady and variable time histories.

"Precisely defined" wall shearing stresses means that their magnitude generated at any point and time on the surface of the substrate in the confined measuring volume is known within a measuring uncertainty (mean error) of less than 10%. Depending on desired application, these distributions can have different spatial and temporal features as hereafter shown.

SUMMARY OF THE INVENTION

The invention provides an engineering method and apparatus for generating an axial-symmetric rotation of fluid while simultaneously removing a defined fluid volume in the center of a rotational axis and causing it to be recirculated or collected With substituted fluid volume returned to the measuring volume instead.

The apparatus to achieve this goal consists of a housing in the form of a large diameter tube closed on top with a lid. Beneath this lid a stirrer is inserted in the center with its diameter smaller than the inner diameter of the housing. The stirrer is attached to a rotating hollow axis, through which fluid is removed from the enclosed measuring volume, circulated by a pump and returned to the closed measuring volume through at least one return opening in the lid or elsewhere. Depending on application, the bottom of the apparatus is either open (field deployment) so that the substrate/fluid interface is that of the original sediment or it is sealed and the interface is that of an inserted sediment core or of any other desired substrate surface.

BRIEF DESCRIPTION OF THE DRAWINGS

The invention may be best understood by those having ordinary skill in the art by reference to the following detailed description when considered in conjunction with the accompanying drawings in which.

DETAILED DESCRIPTION OF THE INVENTION

Figure 1:
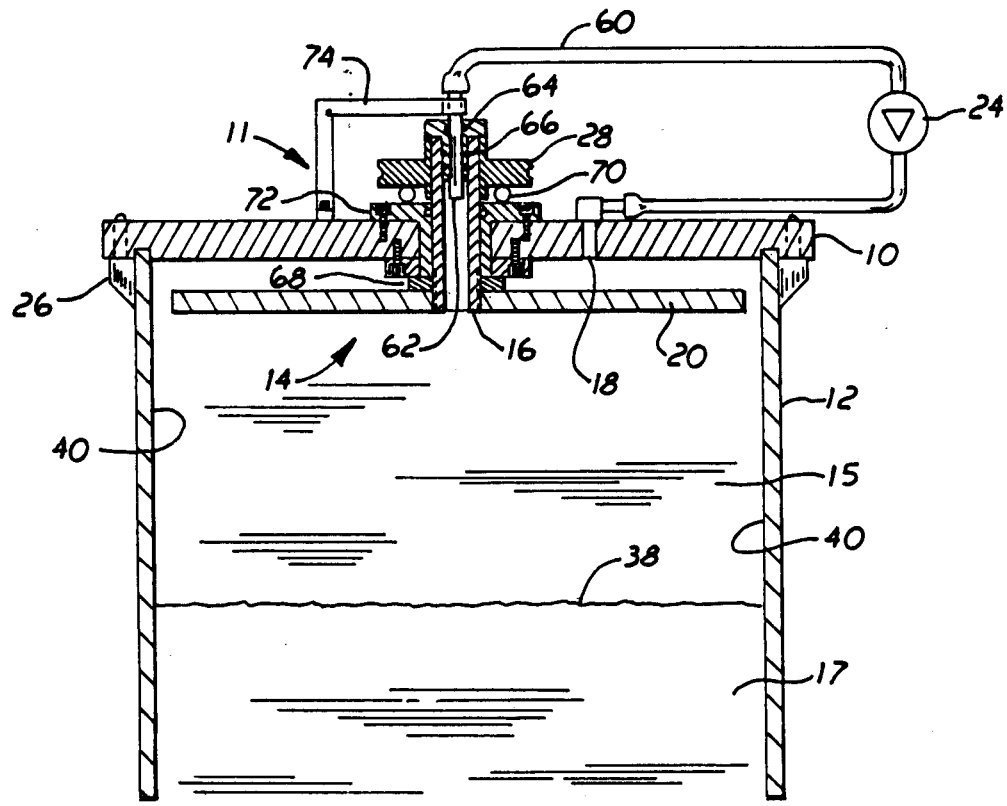
FIG. 1 is a cross-sectional elevation view of one particular feature of the invention.

The apparatus 11 of FIG. 1 consists of a circular housing 12 which is open at the bottom and closed by a lid 10 on top. Lid 10 is connected to housing 12 via a hinge 26 which permits a hinged-type opening and closing.

Beneath lid 10 a stirrer device 14 is attached which consists of a circular disk 20. Disk 20 is connected to a hollow stem 16 which can rotate freely in the lid 10 yet is sealed. The stem 16 is driven by a drive wheel 28 attached outside the lid 10.

The hollow rotating stem 16 is coupled to a polyvinyl chloride or like plastic tubing 60 which leads to a pump 24, whose outlet side is connected to a return opening 18 located close to the center of the lid 10.

Figure 6:
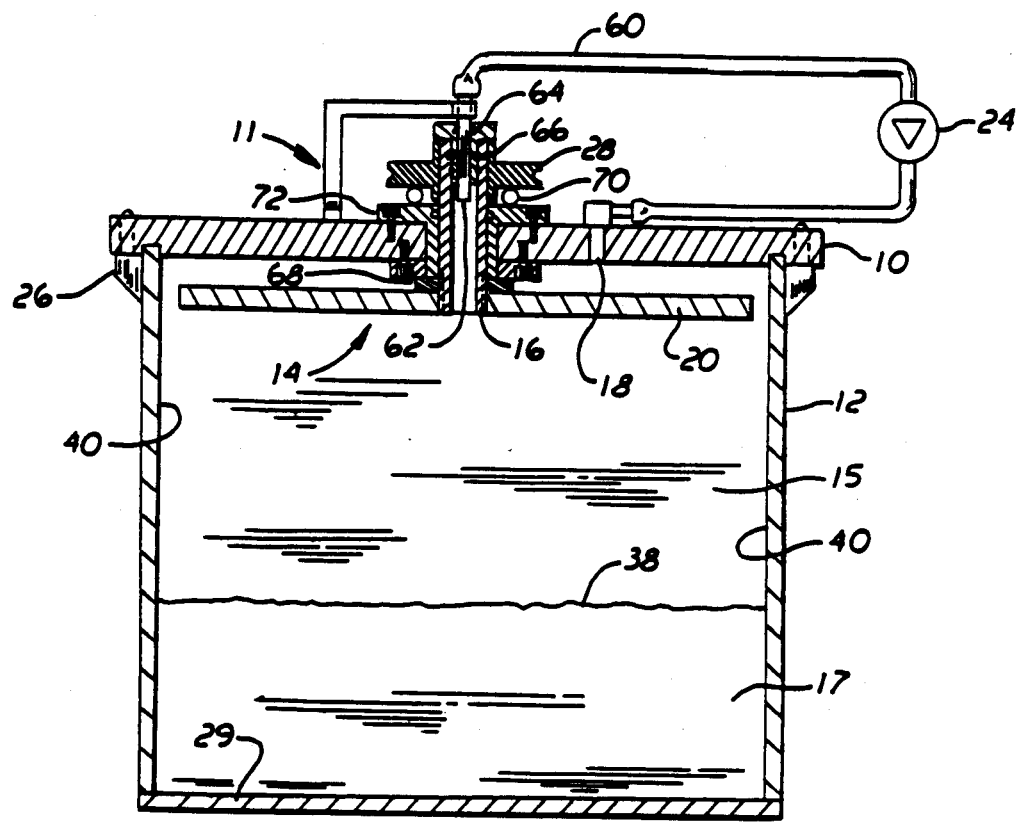
FIG. 6 is a view of the device of FIG. 1 with a bottom sealing member.

Apparatus 11 can have a bottom member 29 when used to collect microbiological matter growing in a culture medium. See FIG. 6. In the apparatus 11 or 11a the stirrer device 14 or 14a is connected to a stainless steel tube 62 which in turn leads to the tubing 60. The connection of stirrer device 14 or 14a to the steel tube 62 is made by inside 64 and outside 66 0-rings. An acrylic counter-nut 68 secures disk 20 at the end of stem 16. Glass ball bearings 70 separate the drive wheel 28 from the top sealing block 72 usually made out of TEFLON ®. Brace 74 prevents steel tube 62 from turning When turning the hollow axis 16 via the drive wheel 28 by means of an AC motor and variable gear box (not shown), the stirrer device 14 is also turning. This in turn generates a fluid flow relative to the axis of apparatus 11. The rotation of the stirrer device 14 produces a rotating flow of the fluid inside the confined volume, with the velocity vector decreasing in magnitude in radial direction from the outer diameter towards the center. The stirrer device 14 thus generates a non-homogeneous wall shearing stress at the substrate/fluid interface 38 which decreases accordingly in magnitude from larger to smaller radii. When fluid 15 is removed simultaneously through the hollow stem 16, a further flow component is generated which increases from larger to smaller radii in the wall boundary layer With appropriate dimensions (see Examples below) for the tube housing 12 and stirrer device 14, together with a proper combination of fluid volume recirculated per unit time and angular velocity of the stirrer device 14 it is possible to generate a flow field which leads to a spatially homogeneous field of near-bottom velocity gradients and thus to a spatially homogeneous magnitude of the wall shearing stress (but not in direction) at the substrate/fluid interface 38 inside the apparatus between fluid 15 and substrate 17. Other combinations of angular velocity of stirrer device 14 and center-removed recirculated fluid produce radially increasing or decreasing wall shearing stress distributions. These alternate combinations are desirable for selected applications.

The individual applications can be grouped into laboratory devices and field devices, and within these groups as either flux chambers or samplers. In all cases the wall shearing stress fields can be either spatially homogeneous or inhomogeneous, with their time histories then being steady-state, step functions from high to low or from low to high or variable. The combinations of angular velocity of the stirrer and simultaneous fluid recirculation can be manually selected for the simple temporal steady-state distributions. For step functions in time, or for variable time histories such as cycling in general or tidal cycle simulations specifically, or for adjustment of the wall shearing stress field inside a chamber deployed in-situ to values measured on the outside in the unconfined boundary layer, digital electronics for driving pump and stirring device 14 are required. Also needed is a computer program utilizing a pre-established calibration matrix stored in a microprocessor to select the required stirring/pumping rate combinations.

Figure 2:
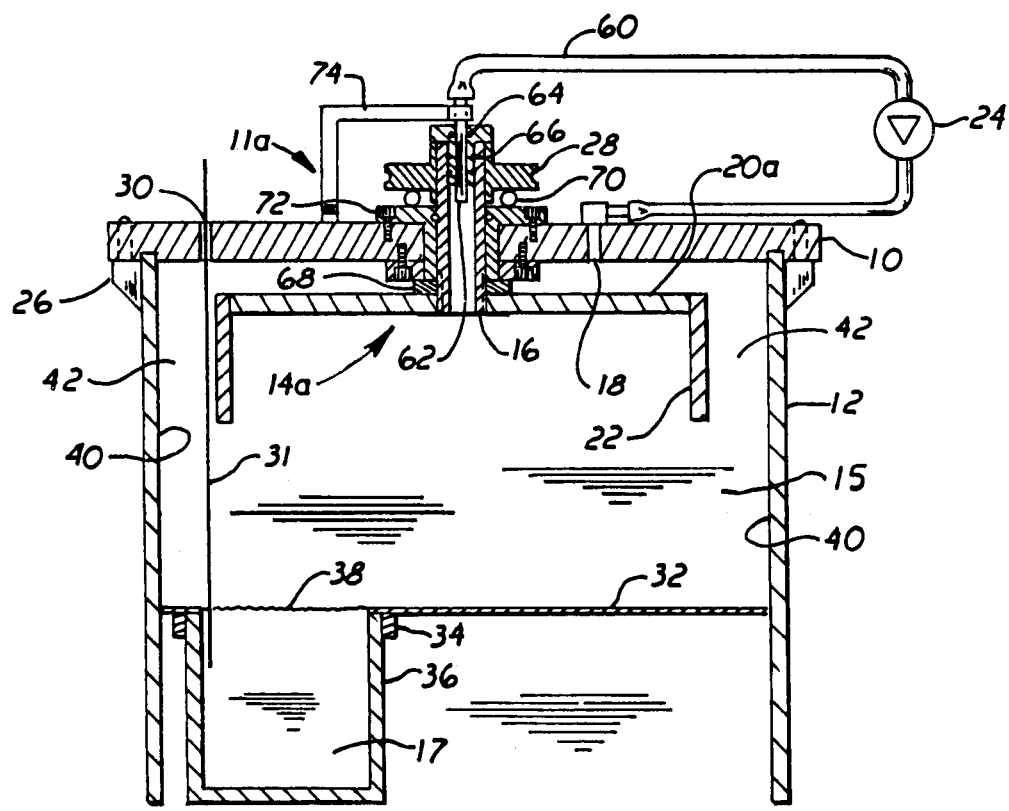
FIG. 2 is a cross sectional elevation view of a second feature of the invention.
Figure 3:
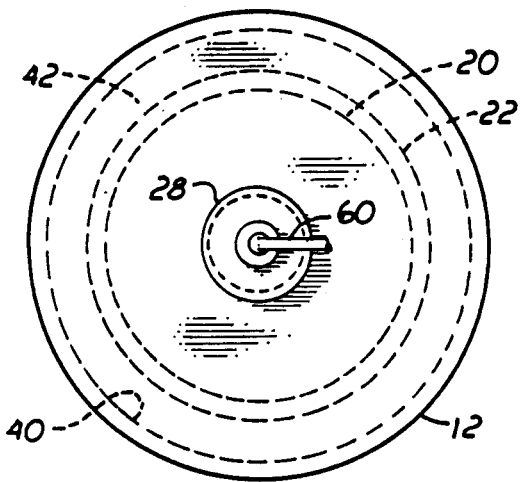
FIG. 3 is a top plan view of a circular housing of the invention.
Figure 4:
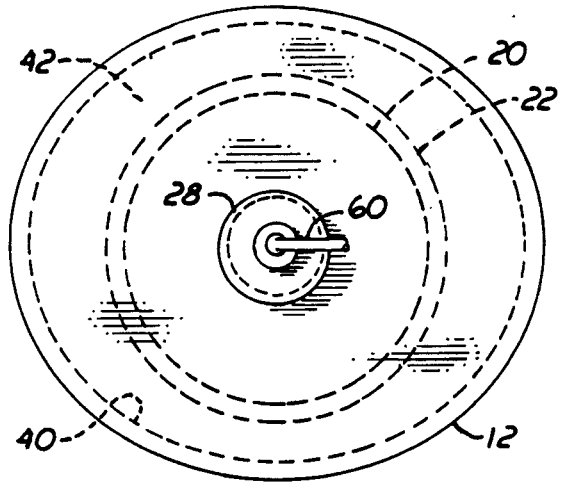
FIG. 4 is a top plan view of an elliptical housing of the invention.

In the feature shown in FIG. 2, a skirt 22 is attached to a shortened circular disk 20a which is aligned parallel with the side wall 40 of housing 12 but at a considerable distance from it. It permits the introduction of probing devices 31 through feed-through openings 30 in the lid 10 into the space between the skirt-equipped stirrer disk 20a and the housing side wall 40 such that measurements can be taken of the fluid 15 and substrate 17 in the confined area. In this feature the invention uses the Couette flow generated between the skirt 22 and the sidewall 40 of the housing to extend the stirrer device 14a by a liquid addition all the way to the sidewall 40, since the Couette flow established in the circular gap 42 generates a constant fluid shearing stress in radial direction. This permits the boundary layer at the substrate/fluid interface underneath this gap 42 area to experience the same magnitude of the wall shearing stress as underneath the solid-material stirring device 14a at smaller radii. In this feature the stirrer device 14a is thus partly solid material, partly fluid and generates the same effect regarding the magnitude of the wall shearing stress as if a solid disk 20 extends to the sidewalls of the housing 12 as shown in FIG. 1. At high turning rates a Taylor-Couette flow is generated with different fluid shear stress patterns but similar effect on the interfacial boundary layer.

The shape of the disk 20 or 20a has to be selected based on experiment-specific requirements. For example, it may be necessary to use a disk with wedge-type radial cross section, either convergent or divergent. Furthermore, the stirrer device 14 or 14a can be formed by radially attached wings or blades. Also, a perforated or a grid-like disk is feasible. The stirrer can even be shaped like a bell.

The tube housing 12 has a circular shape when a spatially homogeneous wall shearing stress has to be generated at the substrate/fluid interface. If a non-homogeneous wall shearing stress field of known radial distribution has to be generated at the substrate/fluid interface instead, other cross-sectional, for example, elliptical shapes of the housing may be chosen.

Furthermore, precisely known inhomogeneous fields of the wall shearing stress increasing or decreasing in radial direction can be generated either by a different selection of the amount of water volume removed centrally and recirculated per unit time or by a different selection of the number of rotations of the stirrer per unit time compared to the combination setting of stirring device revolutions and recirculated fluid volume per minute for spatially homogeneous distributions.

When using the device as a laboratory simulator, it has to be built in a way that it can contain a substrate 17 of approximately twenty cm depth with an overlying fluid 15 column of approximately ten cm height. Furthermore, a bottom lid 29 has to be present which needs to be movable sideways for sealing and be removable when sediment cores are collected in the field.

Figure 5:
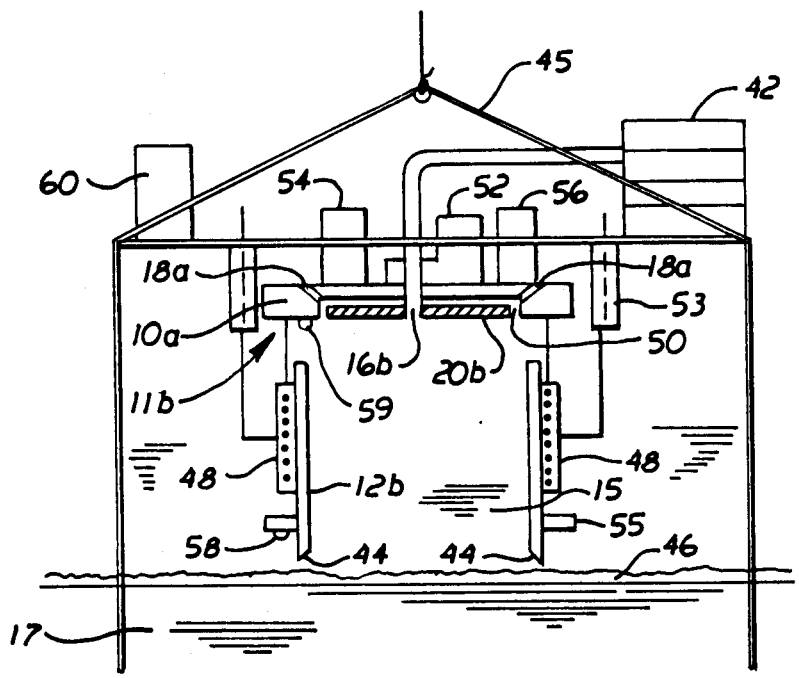
FIG. 5 is a cross sectional elevation view of a third feature of the invention.

For field investigations the apparatus 11b as seen in FIG. 5 has to be built such that it can be deployed in free-fall mode or via cable from a vessel to land on the ocean floor. In this case no bottom lid 29 is necessary to seal the apparatus 11b unless sediment cores are to be recovered after the measurements.

The apparatus 11b in FIG. 5 is supported by a superstructure 45 in which is suspended apparatus 11b by bleeders 53. Disk 20b is attached to the hollow stem 16b leading to a rosette sampler 42 with base and motor drive. The housing 12b has a sharp bottom rim 44 to penetrate the sea floor 17. A layer of marine snow (organic-rich detritus) 46 rests on the sea floor 17. Circumferentially attached bleeders 48 are employed for closing lid 10a which has a recess 50 for the rotating disk 20b. Underwater housing 52 with gear box, drive shaft and motor rests on the lid 10a along with other equipment such as underwater camera 54, pressure housing with electronics 56 and power pack 60. Vent holes or fluid replacement holes 18a are located on the circumference of recess 50.

The superstructure 45 is lowered to the sea floor by a cable and thereafter housing 11b settles using bleeders 53 until rim 44 is imbedded in the sea floor 17 to the depth of collar 55. The bottom switch 58 underneath collar 55 then activates the closing of the lid via bleeders 48. Switch 59 attached to lid 10a activates upon closing of disk 20b which causes sea water rotation in the now confined volume 15 for generation of a wall shearing stress field. Under its influence the marine snow 46 accumulates in the center of apparatus 11b. A timed valve activates suction of fluid 15 through hollow stem 16b into the rosette sampler. Additional samples are then activated through electronics 56 along with the camera 54. The device returns to the surface for analysis of the samples after completed collection cycle.

The apparatus of this invention can be used for investigation of either the effects of precisely known wall shearing stresses generated at the substrate/fluid interface by certain combinations of rotational speed of the stirrer device 14 and the amount of water removed simultaneously through the center stem 16 or 16a and recirculated per unit time, or for sampling or concentration measurements of the sediment particles and aggregates which might be eroded under this wall shearing stress. In the latter case, the pump recirculation path requires equipment to filter out these sediment particles and aggregates or to collect the fluid. Such devices filtering out sediment or aggregates eroded at a pre-set bottom stress are also necessary when the task is to investigate the remaining sediment/porewater system.

The bottom material inside the device can be any type of finely ground material with porewater space or even a solid, impermeable plate either flat or with a rough surface. Substrates for bacterial growth can also be employed.

The fluid can be any chemical or chemical solution as long as the materials of the design ensure its confinement. Entrainment of porewater solutes, biomass and their exudates under selected bottom stress fields are also possible beyond sediment entrainment studies with adequate filters or fluid samplers in the recirculation path. The recirculation path does not need to be closed. Water could be removed in controlled volumes from the sealed housing through the hollow axis 16 and fed to other processing units, while the replacement fluid is transported by another (synchronized) second pump into the housing via one or several return openings. Recirculated or replaced fluid can also provide a "spike" of fluid with new characteristics, e.g. strongly reducing or with special chemicals before returning to the enclosed fluid volume inside the apparatus. Also, the substrate/fluid interface does not need to be discontinuous, but can form a strong density gradient like in fluid mud.

In FIG. 2, a feature is shown where the false bottom 32 of the device is equipped With a receptacle 34 for a sediment core liner 36 sealed at the bottom. The diameter of the receptacle 34 is thus smaller than the radius of the false bottom plate 32. In this feature it is possible to investigate recovered sediment cores in a simple manner in a laboratory, either on land or shipborne.

The proposed device is especially well adapted for investigations of processes at the sediment/water interface of natural water systems. However, a wide variety of additional applications is possible. For example, in microbiological manufacturing procedures it is desirable that microbiologic populations, whose metabolic products are harvested, are exposed to a controlled and precisely known flow velocity and thus wall shearing stress. Other examples can be found in process engineering, especially when a well defined vertical flux of materials has to be achieved between a fluid and a substrate. This latter case bears relevance for surface coatings.

For the fluid it is not necessary to be water. It even may be air or other gases, carrying atomized metals, aerosols or be other diluted two-phase systems of which one phase is settling on the substrate surface in rates controlled by the wall shearing stress. The apparatus and method also can be used to generate radial pressure distribution and capillary flow exchange in porous media such as sandy sediments.

EXAMPLES 1-8

Particular examples of an apparatus utilizing the invention are described below In each of the below listed examples the apparatus 11 has the following dimensions:

diameter of housing: 30 cm
housing height: 35 cm
substrate depth: 25 cm
water height from interface to lid: 10 cm
total confined water volume: 7 liters
total confined sediment volume: 18 liters (depending on insertion technique)
disk with skirt, diameter: 20 cm
disk with skirt, length: 4.5 cm The following combinations of stirrer rotations/fluid volume recirculation shown below generate homogeneous wall shearing stresses (expressed by the friction velocity $u^* = (\tau\rho)$ where $\rho$ = fluid density) of defined magnitude over the interfacial area with errors <10% for above dimensions:

| friction velocity $u^*$ (in cm/s) | rotation of disk with skirt | fluid volume recirculated (in mm/min) |
| --- | --- | --- |
| (1) 0.22 | 5 rev. in 67 sec. | 95 |
| (2) 0.30 | 6 rev. in 67.5 sec. | 150 |
| (3) 0.37 | 7 rev. in 60 sec. | 365 |
| (4) 0.50 | 13 rev. in 58 sec. | 195 |
| (5) 0.54 | 13 rev. in 60 sec. | 424 |
| (6) 0.69 | 20 rev. in 60 sec. | 230 |
| (7) 0.75 | 23 rev. in 60 sec. | 290 |
| (8) 1.00 | 30 rev. in 60 sec. | 680 |

$u^*$ = friction velocity
$\tau$ = wall shearing stress
$\rho$ = fluid density

EXAMPLES 9-12

Examples producing homogeneous and inhomogeneous wall shearing stresses of defined magnitude over the interfacial area for an apparatus with 12 cm diameter and 5 cm water depth:

| $u^*$ (cm/s) | rotation of flat disk | fluid volume recirculated (cm/min) |
| --- | --- | --- |
| (9) homogeneous, 0.25 | 10 rev. in 60 sec. | 67 |
| (10) homogenous, 0.4 | 17.2 rev. in 60 sec. | 90 |
| (11) maximum at outside radius: 0.45 minimum at center: 0.13 | 17.3 rev. in 60 sec. | no pumping |
| (12) minimum at outside radius: 0.3 maximum at center 2.2 | 17.1 rev. in 60 sec. | 1000 |

The above procedure and apparatus were used with substrate and fluid column in reverse and sidewise position in a confined space. Substantially the same results set forth in the above Examples 1-8 were achieved. Therefore, the apparatus and method functions independently of the relative position of fluid column and substrate.

Having thus described the invention, what is claimed and desired to be secured by Letters Patent is:

1. Method of generating wall shearing stress fields of exact magnitude at a substrate/fluid interface with exact time histories comprising rotating a disk within a confined space containing a substrate and a fluid column to generate a fluid flow moving rotationally around a center axis of the confined space while simultaneously removing by suction a metered fluid within the center axis and replacing the fluid in the confined space.

2. Method according to claim 1, wherein the substrate is a sediment and the fluid is sea water, and the sediment/water interface is investigated in respect to physical, chemical, sedimentological and biological processes.

3. Method according to claim 1 wherein the removed fluid is recirculated through a pump to the confined space.

4. Method according to claim 1 wherein the disk diameter is slightly smaller than the inside diameter of the confined space.

5. Method according to claim 1 wherein the disk edge has a circumscribing descending skirt.

6. Method according to claim 1 wherein the substrate is a biological medium and the fluid is compatible with microbiological life form.

7. Method according to claim 1 wherein the metered fluid is collected and removed from the confined space through an orifice in a center of the disk and replaced in the confined space with a fluid from an alternate source in the same quantity as the fluid collected.

8. Method of generating wall shearing stress fields of exact magnitude in a substrate/fluid interface comprising:
 a. mounting a rotatable disk within a confined space containing a substrate with an overlying column of fluid
 b. turning the disk within the fluid while simultaneously sucking fluid through an opening in the center of the disk, and
 c. recirculating the fluid sucked from the confined space, back to the confined space through a hole in a lid forming a top of the confined space.

* * * * *